United States Patent [19]

Crane et al.

[11] Patent Number: 4,606,825
[45] Date of Patent: Aug. 19, 1986

[54] PURIFICATION OF IMMUNOGLOBULIN G

[75] Inventors: Laura J. Crane, Long Valley; David R. Nau, Lebanon, both of N.J.

[73] Assignee: J. T. Baker Chemical Company, Phillipsburg, N.J.

[21] Appl. No.: 725,660

[22] Filed: Apr. 22, 1985

[51] Int. Cl.⁴ .............................................. B01D 15/08
[52] U.S. Cl. .................................... 210/635; 210/656; 210/927
[58] Field of Search ..................... 210/635, 656, 927

[56] References Cited

U.S. PATENT DOCUMENTS

| | | | |
|---|---|---|---|
| 4,464,165 | 8/1984 | Pozzaad, Jr. | 210/635 |
| 4,468,330 | 8/1984 | Kamirama | 210/656 |
| 4,529,711 | 7/1985 | Fukano et al. | 210/927 |
| 4,544,485 | 10/1985 | Pinkerton et al. | 210/635 |

*Primary Examiner*—John Adee
*Attorney, Agent, or Firm*—George W. Rauchfuss, Jr.; Salvatore R. Conte

[57] ABSTRACT

A method of separating and recovering immunoglobulin G from biological fluids by liquid chromatographic or solid phase extraction processes utilizing, as the solid phase, a carboxylated form of silica gel or controlled pore glass bearing non-cross-linked covalently bound polyethylenimine functions.

12 Claims, No Drawings

PURIFICATION OF IMMUNOGLOBULIN G

BRIEF DESCRIPTION OF INVENTION

In accordance with the present invention, a carboxylated form of the covalently bound, non-cross-linked polyethylenimine reaction product of particulate silica gel having an average particle diameter of from about 3 to about 70 microns and an average pore size of from about 50 to about 1000 Angstrom units, or particulate controlled pore glass having an average particle diameter of from about 37 to about 177 microns and an average pore size of from about 40 to about 1000 Angstrom units, with polyethyleniminopropyl trimethoxy silane having an average molecular weight of from about 400 to about 1800, is utilized as the solid phase in chromatographic or extraction processes to obtain substantially purified immunoglobulin G from biological fluids.

PRIOR ART

In U.S. Pat. No. 4,469,630 of M. Flashner, entitled "Purification of Monoclonal Antibodies", the purification of monoclonal antibody type IgG is described using the non-carboxylated form of the above-described covalently bound, non-crosslinked polyethylenimine reaction product. It has now been surprisingly found that the carboxylated form of said reaction product, which forms a cation exchange matrix, effectively and selectively binds the IgG antibodies are present in biological fluids. Furthermore, whereas the non-carboxylated anion exchange matrix described in U.S. Pat. No. 4,469,630 binds most of the ascites fluid proteins, then selectively separates the IgG antibody, the carboxylated cation exchange matrix herein employed binds primarily the IgG antibody, leaving most of the other proteinaceous material in the biological fluid unbound. It is very unusual, and not to be predicted, that a protein will bind to both an anionic (positively charged) and a cationic (negatively charged) matrix in essentially the same pH range.

DETAILED DESCRIPTION OF THE INVENTION

The invention relates, in its preferred embodiment, to a method of separating and purifying immunoglobulin G (IgG) antibody from biological fluids containing same utilizing liquid column chromatography on a particular stationary porous phase of a carboxylated form of silica gel or controlled pore glass (CPG) bearing non cross-linked covalently bound polyethylenimine (PEI) functions and gradient elution of the IgG antibody from the carboxylated polyethylenimine bound silica gel or CPG column with aqueous buffer of from about pH 5.5 to about pH 8.3. The invention also relates to a method of separating and purifying said IgG antibody from biological fluids utilizing solid phase extraction means with said carboxylated material as the solid phase matrix.

The particular carboxylated form of silica gel bearing non-crosslinked covalently bound polyethylenimine functions, hereinafter sometimes referred to as "carboxylated-PEI-PrSi-silica gel", and the particular carboxylated form of controlled pore glass bearing non-crosslinked covalently bound polyethylenimine functions, hereinafter sometimes referred to as "carboxylated-PEI-PrSi-CPG", for purposes of convenience, which are utilized in this invention, are described in copending U.S. patent application Ser. No. 555,368, filed by Hugh Ramsden and entitled "Polyethylenimine Bound Chromatographic Packing", the content of which is incorporated herein by reference. Relevant text of this application is reproduced below.

Excerpt from Ramsden's U.S. patent application Ser. No. 355,368.

"The non-crosslinked covalently bound PEI silica gel and glass products of the present invention are conveniently prepared in accordance with the following steps:

A. reacting either particulate silica gel having an average particle diameter of from about 3 to about 70 microns and an average pore size of from about 50 to about 1000 Angstrom units, or particulate controlled pore glass having an average particle diameter of from about 37 to 177 microns and an average pore size of from about 40 to about 1000 Angstroms, in an inert organic solvent slurry with a lower alkanolic solution of polyethyleniminopropyl trimethoxy silane having an average molecular weight of from about 400 to about 1800, said reaction being conducted at ambient to refluxing temperature for about 2 to about 50 hours;

B. recovering the resultant solid fraction from the reaction mixture; and

C. heating said solid fraction at a temperature and for a time sufficient to dry and completely bond the silane to the respective silica gel or controlled pore glass.

As used herein, the term "covalently bound" or "covalently bonded" means that the PEI moieties are covalently attached to the silica gel or controlled pore glass by way of chemical interaction resulting in a propyl-silyl (Pr-Si) linkage; and the term "non-crosslinked" means that the imino and amino groups on adjacent covalently bound PEI moieties are not cross-linked, or reacted with a crosslinking agent, to form a polymeric layer.

Without being bound thereby, it is believed that the reaction proceeds to completion in two steps as follows:

Step 1: Silica hydroxyls and the methoxy groups on the silane react to form Si-O-Si bonds and free methanol, with some residual methoxy groups remaining unreacted:

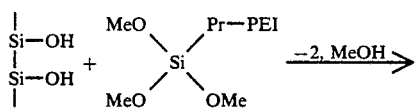

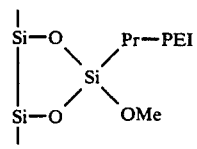

Step 2: Completion of the reaction with the residual methoxy groups is effected during heat curing by (a) and (b);

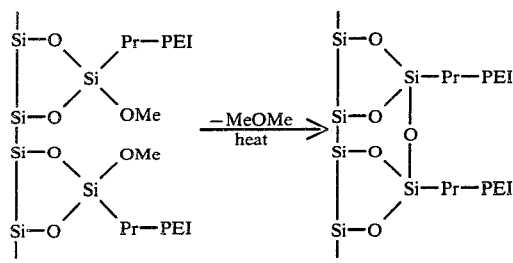

(a)

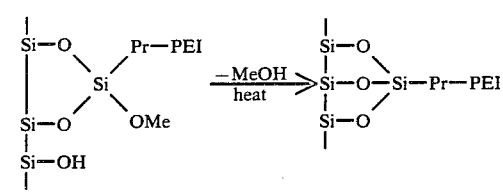

(b)

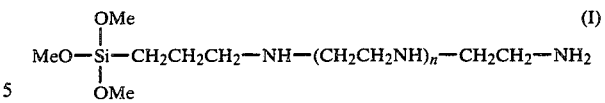

$$MeO-\underset{\underset{OMe}{|}}{\overset{\overset{OMe}{|}}{Si}}-CH_2CH_2CH_2-NH-(CH_2CH_2NH)_n-CH_2CH_2-NH_2 \quad (I)$$

wherein, for purposes of this invention, n is an integer from about 4 to about 37, or, if expressed in terms of average molecular weight, from about 400 to about 1800.

The silane (I) is used in the reaction with the silica gel or CPG in the form of a lower $C_1$-$C_6$ alkanolic solution using sufficient alkanol to solubilize the silane. A fifty percent w/w isopropanolic solution is preferred. In general, about 25–100 grams of the silane, or, alternatively, about 50–200 ml of a fifty percent w/w alkanolic solution of the silane, is used to react with each 100 grams silica gel or CPG. The reaction may be conducted at ambient temperature although elevated temperatures up to the refluxing temperature of the reaction solvent system may be utilized to enhance the rate of reaction. The reaction proceeds readily to substantial completion (Step 1) within 2–50 hours. Stirring during admixture of the reactants is advantageously employed although the reaction thereafter may continue without further stirring. Anhydrous conditions are not critical, it having been found that the presence of a small amount of water, for example, about 0.1–1.0 ml per 50 ml of the slurry solvent, does not adversely affect the reaction.

The resultant solid fraction is recovered from the reaction mixture by conventional physical means, for example, filtration, centrifugation, etc. In general, a filtering means sufficient to retain a particle size of 5 microns is suitable whereas centrifuging is suitable for a particle size of 3 microns.

The recovered solid fraction is then heat cured at a temperature and for a time sufficient to dry and completely bond the silane to the silica gel or CPG covalently. In general, from about 1–4 hours at about 40°–120° C. has been found sufficient. The thus-obtained covalently bound, non-crosslinked final product preferably contains from about 0.5 to about 3.8 percent nitrogen.

The thus-obtained weakly basic PEI-PrSi-silica gel or PEI-PrSi-CPG products may be converted to a weakly acidic carboxylated form by conventional treatment, for example, see S. Gupta et al., Anal. Biochem. 128, 196–201 (1983), with an appropriate dibasic acid anhydride in an inert organic solvent. Typical such anhydrides include, for example, succinic acid anhydride, glutaric acid anhydride, diglycolic acid anhydride and the like. Sufficient anhydride is used to react with substantially all of the imino and amino functions on the PEI moiety. The number of carboxylic groups in the resultant succinoylated product, for example, may be determined by standard titration against suitable alkali. For purposes of this invention, a carboxyl milliequivalent per gram of final product from about 0.3 to about 1.2 is preferred."

End of Excerpt

Silica gel, consisting of amorphous silica, is commercially available in irregular and spherical (preferred) particulate forms and in several commerical grades with mesh sizes ranging from 3 through 325 (ASTM). Rather than relying upon a numerical indication of mesh size, however, more accurate indicia for purposes of this invention are the average diameter and average pore size of the silica gel particles, respectively, from about 3 to about 70 microns and from about 50 to about 1000, preferably 250–500, Angstrom units. For end product use in packing HPLC chromatographic columns, a silica gel starting material of from about 3 to about 10 microns is preferred, and, for packing low pressure chromatographic columns, from about 40 to about 70 microns is preferred.

Controlled pore glass (CPG), which is a silicate containing support material chemically similar to silica for use in liquid chromatography, is commercially available, for example, from the Pierce Chemical Co., Rockford, Ill., with average particle diameter of 37–177 microns and average pore size of 40–1000 Angstroms, preferably 40–500 Angstrons.

Among the inert organic solvents suitable for preparing the silica gel or CPG slurry are aliphatic hydrocarbons such as, for example, hexane, heptane and the like; aromatic hydrocarbons such as, for example, benzene, toluene, xylene and the like; lower alkanols such as, for example, ethanol, isopropanol, butanol and the like; chlorinated methanes such as, for example, methylene chloride, chloroform, carbon tetrachloride and the like (Caution: such chloro solvents may react at higher temperatures!); and such other inert solvents as tetrahydrofuran, glyme, diglyme and the like. In general a 1:5 ratio of silica gel or CPG in grams to solvent in milliliters affords a suitable slurry. Due to the fine, insoluble nature of the particulate silica gel and CPG, a slurry rather than a true solution is obtained.

Polyethyleniminopropyl trimethoxy silane, also known as (N-trimethoxysilylpropyl)-polyethylenimine, is the reaction product of polyethylenimine and aminopropyltrimethoxy silane and can be represented by the following formula:

The aforementioned weakly acidic carboxylated-PEI-PrSi-silica gel and carboxylated-PEI-PrSi-CPG products of Ramsden, which are the N-acylated reaction products of a dibasic acid anhydride such as, for example, succinic acid anhydride (preferred), glutaric acid anhydride, diglycolic acid anhydride and the like, with the imino and amino functions on the PEI moiety of the PEI-PrSi-silica gel or PEI-PrSi-CPG, are the solid phase materials utilized in the chromatographic and extraction methods of purification of this invention.

Said carboxylated products of Ramsden are those wherein the starting silica gel has an average particle diameter of from about 3 to about 70 microns and an average pore size of from about 50 to about 1000 Angstrom units, preferably about 250–500 Angstroms; wherein the starting controlled pore glass (CPG) has an average particle diameter of from about 37 to about 177 microns and an average pore size of from about 40 to about 1000 Angstrom units, preferably about 40–500 Angstroms; wherein the starting polyethyleniminopropyl trimethoxy silane, which is subsequently bound to the particulate silica gel or the particulate CPG in covalently bound non-cross-linked form, has an average molecular weight of from about 400 to about 1800; and wherein the residual carboxylic acid functionality of the dibasic acid segment (the carboxyl of said segment being terminall located) attached to the imino and amino functions on the PEI moiety preferably provides a carboxyl milliequivalent per gram of carboxylated-PEI-PrSi-silica gel or carboxylated-PEI-PrSi-CPG product of about 0.3–1.2.

Accordingly, the instant invention provides a method of obtaining substantially purified immunoglobulin G, also known as antibody type IgG, from a biological fluid containing same, such as, for example, plasma, serum, supernatent fluid from tissue culture cells producing IgG antibody, ascites fluid and the like, by employing either liquid chromatography or solid phase extraction wherein the liquid chromatographic packing or the solid phase extraction matrix comprises said particulate carboxylated-PEI-PrSi-silica gel or carboxylated-PEI-PrSi-CPG.

It has now been found that such chromatographic packing or solid phase matrix is particularly useful in liquid chromatography and solid phase extraction for preferentially (selectively) binding IgG antibodies and removing it from most other proteins in the biological fluid. The bound IgG antibody may then be eluted from the solid phase matrix in substantially purified from, or may be further separated and purified from the small amount of other bound protein in liquid chromatography, by gradient elution using appropriate aqueous buffers. As used herein "substantially purified" means that greater than 70% of the protein present in the quantitatively recovered IgG antibody fraction is the IgG antibody. Indeed, in the preferred process of this invention, liquid chromatography, more than 90% of the protein, i.e., essential homogeneity, in the quantitatively recovered IgG antibody fraction is the IgG antibody. The percent purity may be verified by known procedures in the art, such as, for example, by sodium dodecyl sulfate polyacrylamide gel electrophoresis; see U. K. Laemmli, Nature, 227, 680 (1970).

The instant invention is suitable for use with biological fluids containing IgG antibody such as, for example, plasma, serum, tissue culture supernatant, ascites fluid (e.g., mouse or rat ascites fluid) and the like. The term "immunoglobulin G" or "IgG antibody" includes all monoclonal and polyclonal IgG antibodies and subclasses of the IgG type, for example, $IgG_1$, $IgG_{2a}$, $IgG_{2b}$, $IgG_3$, $IgG_{1+3}$ and the like. The methodology of preparing such liquids or solutions or substances containing antibody is common to the art, for example, see "Monoclonal Antibodies, Hybridomas; A New Dimension in Biological Analyses", by R. H. Kennet et al., published by Plenum Press, New York, 1980; and "Methods in Enzymology" by G. Galfred and C. Milstein, edited by J. J. Langone and H. Van Vunakis, Vol. 73, p. 31–46, published by Academic Press, 1981.

The isolation of IgG antibody in highly purified form is obviously desirable. For example, for in vivo therapeutic purposes, IgG antibody as pure and as concentrated as possible is required to minimize adverse side effects and to maximize the intended therapeutic purpose. Similarly, for in vitro diagnostic purposes, such purified and concentrated antibody is desirable to maximize the sensitivity and specificity of the particular diagnostic test.

Preferably, the biological fluid containing IgG antibody is pre-treated to remove interfering particulate matter and is equilibrated to the appropriate ionic strength and pH necessary to achieve binding of the IgG antibody to the carboxylated-PEI-PrSi-silica gel or carboxylated-PEI-PrSi-CPG solid phase material. The interfering particulate matter can be removed by conventional clarifying means, for example, by filtration or by centrifugation at a force sufficient to pelletize the particulate material. Equilibration of the biological fluid can be achieved by any means common to the state-of-the-art, for example, by chromatographic desalting with an appropriate buffer on molecular sieves of appropriate type and pore size such as those commercially available under the brand name "Sephadex", by dilution with or dialysis against an appropriate buffer, and the like, to equilibrate the biological fluid to a pH less than the pH (that pH at which the monoclonal antibody carries no net ionic charge in its environment) of the particular IgG antibody but no lower than pH 5.5 and to an ionic strength equal to or less than the ionic strength of the lower ionic strength buffer used for elution in the subsequent treatment of the biological fluid.

For the purification by liquid chromatography to essential homogeneity, chromatographic columns suitable for use in liquid chromatography are packed with the previously described carboxylated-PEI-PrSi-silica gel or carboxylated-PEI-PrSi-CPG porous chromatographic matrix. Suitable steel or glass chromatographic columns include those having dimensions of about 5–100 cm in length and internal diameters of about 1–100 mm. Selection of the proper chromatographic parameters such as, for example, column packing technique, column size, column temperature, pressure and the like, are readily determined by one of ordinary skill in the art.

The packed column is equilibrated in a chromatograph by passing an appropriate buffer solution through the column. After this buffer-equilibration step, the column is used to make the chromatographic separation of the proteinaceous components of the biological fluid which, as noted, may have been previously freed of particulate matter and equilibrated to the appropriate ionic strength and pH. A sample of the biological fluid is applied to the buffer-equilibrated column to selectively bind the IgG antibody and minor contaminating proteins to the respective carboxylated-PEI-PrSi-silica gel or carboxylated-PEI-PrSi-CPG chromatographic packing material.

The bound IgG antibody can then be selectively eluted by conventional gradient elution techniques, taking into consideration the interdependent chromatographic parameters of time, flow-rate and gradient shape to generate gradients of increasing ionic strength and/or increasing pH. Cationic buffers, for example, potassium phosphate, tris-acetate, ammonium acetate, sodium chloride and the like, of from about pH 5.5 to about 8.3 can be used to generate such gradients to elute the bound IgG selectively from the carboxylated packing material. For example, the gradient can be advantageously formed from about one-half hour to about four hours with a flow rate of from about 0.1 mL/min to about 2 L/min.

Alternatively, the bound antibody along with minor impurities can be eluted in a single step by a buffer solution of sufficiently high ionic strength to release the bound antibody in substantially purified form. Such a method of selective binding and subsequent single step elution may be described as solid phase extraction, which may be carried out in a column as described above or in a batch process. In the latter, the solid phase matrix of carboxylated-PEI-PrSi-silica gel or carboxylated-PEI-PrSi-CPG is stirred with the equilibrated biological fluid; then the matrix and fluid are separated by conventional means such as decantation or centrifugation, and the IgG antibody is subsequently eluted from the matrix by stirring with an aqueous buffer of appropriate ionic strength to release the bound IgG antibody.

The resolved proteins can be identified by any means common to the state-of-the-art, for example, by monitoring the ultraviolet absorbance at 280 nm. The eluent fractions containing the separated proteins can be collected manually or by use of a fraction collector. The eluent fraction containing the homogeneous IgG antibody can be identified by means well-established in the art such as, for example, by a radioimmunoassay developed for the particular antibody, by other antibody-antigen reactions, or by polyacrylamide gel electrophoresis.

The process of this invention has been found to be independent of the total volume of the biological fluid containing the IgG antibody and there is no limiting factor except for the amount of the carboxylated-PEI-PrSi-silica gel or carboxylated-PEI-PrSi-CPG used as the solid chromatographic packing or solid phase matrix; that is, the process is operable so long as the capacity of the solid support is not surpassed.

In accordance with the method of the present invention, therefore, a biological fluid containing antibody type IgG is separated by liquid chromatography or solid phase extraction to provide said antibody in substantially purified form.

The following Examples are presented to illustrate, but not to limit, the subject invention. Examples 1-5 demonstrate the non-carboxylated reaction products of Ramsden; Examples 6-8 demonstrate the carboxylated reaction products of Ramsden; and Examples 9-11 demonstrate the use of such carboxylated products in the extraction and purification processes of this invention.

EXAMPLE 1

A. To a slurry of 10 grams silica gel with average particle diameter of 40 microns and average pore size of 60 Angstroms, commercially available from J. T. Baker Chemical Co., Phillipsburg, N.J., in irregular form as "Silica Gel #7024", in 50 ml toluene is added with stirring 19.71 grams of a 50% w/w isopropanolic solution of polyethyleniminopropyl trimethoxysilane having an average molecular weight of 400-600 (assume 500), commercially available from Petrarch Systems Inc., Bristol, Pa., as "(N-Trimethoxysilylpropyl)-Polyethylenimine PS076". The mixture is stirred at room temperature (about 25° C.) for about 1 hr. 10 min. and then allowed to stand overnight (about 17 hours) without stirring. Stirring is again initiated for another 5 hr. 40 min. at room temperature and again the mixture is allowed to stand overnight. The mixture is next filtered over a medium fritted glass filter. The filtrate is washed with 50 ml toluene twice and with 50 ml methanol twice to ensure removal of any excess silane reactant and then oven dried at 80°-85° C. for about 3 hr. 30 min. to yield about 12 grams of the covalently bound PEI-silica gel product; about 3.9% N.

B. The procedure of Example I-A is repeated except that 1 ml water is added to the silica gel/silane mixture. The yield of the PEI bonded silica gel product is about 13.3 grams; about 5.5% N.

EXAMPLE 2

A slurry of 20 grams silica gel with average particle diameter of 5.25 microns and average pore size of 330 Angstroms, commercially available from The Sep A Ra Tions Group, Hesperia, CA, as a spherical silica under the trademark "Vydac A", Catalog No. 101T9B5, in 100 ml toluene and 2 ml water is prepared and stirred for 10 minutes at room temperature. To this is added with stirring 39.4 grams of a 50% w/w isopropanolic solution of polyethyleniminopropyl trimethoxy silane having an average molecular weight of 500 and the mixture is stirred for an additional 5 minutes. The mixture is then allowed to stand overnight at room temperature. The mixture is next filtered using a 1.0 microni filter funnel. The filtrate is washed with 50 ml toluene twice and 50 ml methanol twice, then air dried on the funnel and finally oven dried at 80°-85° C. for about 3 hr. 30 min. to yield the PEI bonded silica gel product; about 2.85% N.

EXAMPLE 3

A slurry of 20 grams of 230-400 mesh (ASTM) silica gel having an average particle diameter of 40-63 microns and an average pore size of 420 Angstroms, commercially available from E. Merck Reagents, Germany, under the brand name "Fractosil 500", in 50 ml methanol and 1 ml water is prepared and stirred for 5 minutes at room temperature. A separate solution of 11.2 grams of a 50% w/w isopropanolic solution of polyethyleniminopropyl trimethoxy silane having an average molecular weight of 1800 in 100 ml methanol is also prepared. The silane solution is then added to the silica gel slurry over 5 minutes with stirring. After addition is complete, stirring is discontinued and the mixture is allowed to stand at room temperature for 50 hours. The mixture is next filtered over medium sized sintered glass. The filtrate is washed with 3×50 ml methanol under vacuum and then oven dried at 80°-85° C. for about 4 hours to yield the PEI bound silica gel product; about 1.1% N.

EXAMPLE 4

The following reaction mixtures are prepared in accordance with the teachings of the preceding examples:

| Components | A | B | C |
|---|---|---|---|
| Silica gel (5 microns, 330 Angstroms) | 10 g | 10 g | 10 g |

| Components | A | B | C |
|---|---|---|---|
| Isopropanol | 50 ml | 50 ml | 50 ml |
| Water | 0.5 ml | 0.25 ml | 0.1 ml |
| PEIPr—triMeO—silane (M.W. = 600) as 50% w/w i-PrOH soln. | 9.9 g | 4.95 g | 2 g |

Each reaction mixture is stirred for 5 minutes at room temperature and then allowed to stand without stirring for 41 hr. 30 min. Each mixture is filtered, washed once with 50 ml isopropanol and twice with 50 ml methanol. Each filtrate is oven dried at 80°–85° C. for about 3 hr. 12 min. to yield the respective PEI bound silica gel products; A: 1.2% N; B: 1.0% N; C: 0.9% N.

EXAMPLE 5

A. To a slurry of 10 grams silica gel with average particle diameter of 40 microns and average pore size of 50 Angstroms in 50 ml hexane is added 19.71 grams of a 50% w/w i-PrOH solution of PEIPr-triMeO-silane having an average molecular weight of 500. The mixture is stirred for 5 minutes at room temperature and then heated to reflux temperature for about 2 hours. The mixture is allowed to cool to room temperature, filtered and washed with 50 ml hexane twice and 50 ml methanol twice. The filtrate is then oven dried at 80°–85° for about 3 hours to yield the PEI bound silica gel product.

B. The procedure of Example 5-A is repeated except that an equal amount of controlled pore glass (125 microns, 240 Angstroms) is substituted for the silica gel used therein to yield the corresponding covalently bonded, non-crosslinked PEI-PrSi-CPG product.

EXAMPLE 6

The procedure of Example 2 is repeated except that 25 grams silica gel (5.25 microns; 330 Angstroms) in 125 ml toluene and 2.5 ml water is reacted with 50 grams of the 50% w/w i-PrOH solution of PEIPr-triMeO-silane (M.W. 500) to yield about 29.4 grams of the PEI bonded silica gel product. This product is then mixed with 125 ml toluene and 10 grams succinic anhydride and the mixture rotated in an 80° C. water bath for 2 hours. At the end of this time, 20 ml methanol is added and the mixture is filtered. The recovered succinoylated PEI bound silica gel product is successively washed with 1×50 toluene, 2×50 ml methanol and 1×50 ml ethyl ether. The product is then dried at about 80° C. for about 48 minutes. Titration of the product against 1N sodium hydroxide indicates a carboxyl milliequivalent of about 0.65 per gram of product.

EXAMPLE 7

A. 500 grams of silica gel (40–55 microns; 250 Angstroms) is slurried in 2500 ml of toluene. To this slurry is added 247.5 grams of polyethyleniminopropyl trimethoxy silane (average M.W.=600) as a 50% solution in isopropanol. The mixture is stirred for 15 minutes and then allowed to stand for 48.5 hours at room temperature. The mixture is then filtered and the solid phase washed twice with 1000 ml volumes of toluene followed by two additional washings with 1000 ml volumes of methanol. The washed solid phase is dried and cured in an oven at 85° C. for 5 hours. Yield of PEI-PrSi-silica gel product is about 570 grams.

200 grams of this PEI-PrSi-silica gel product is slurried with 1000 mls of toluene to which 54 grams of succinic anhydride is added. The mixture is placed in a rotary shaker in a 40° C. water bath for 3 hrs. 40 mins. after which 200 mls of methanol are added and the mixture filtered. The thus-obtained succinoylated-PEI-PrSi-silica gel is washed four times with 500 ml volumes of methanol and oven-dried at 85° C. for 3 hours. Yield=217.1 grams. Carboxyl titer =0.65 meq./gram. Analysis: 10.24% C; 1.88% H; and 2.75% N.

B. By following the procedure of Example 7A, except that an equivalent quantity of glutaric acid anhydride and diglycolic acid anhydride is individually substituted for the succinic acid anhydride used therein the corresponding glutaroyl-PEI-PrSi-silica gel and diglycoloyl-PEI-PrSi-silica gel are obtained as respective products.

EXAMPLE 8

To 350 grams of silica gel (15–20 microns; 300 Angstroms) slurried in 1750 mls of isopropanol is added 173 mls of a 50% (w/w) solution of polyethyleniminopropyl trimethoxy silane in isopropanol. The mixture is stirred for 15 minutes and then allowed to stand for 42 hours. The mixture is then filtered and the solids washed twice with 750 ml volumes of isopropanol followed by two additional washings with 750 ml volumes of methanol. The washed solid phase is dried and cured in an oven at 85° C. for 3.5 hours. Yield of PEI-PrSi-silica gel product is about 376.3 grams. Analysis: 1.20% N.

200 grams of this PEI-PrSi-silica gel product is slurried with 1000 mls of toluene and 54 grams of succinic anhydride are added. The mixture is rotated in a 40° C. water bath for 2 hrs. 10 mins. after which 300 mls of methanol are added. The reaction mixture is then filtered and the solid phase is oven-dried at 85° C. for 2 hours to yield about 207.1 grams of the succinoylated-PEI-PrSi-silica gel product (15–20 microns; 300 Angstroms). Carboxyl titer=0.3 meq./gram. Analysis: 5.07% C; 0.95% H; and 1.05% N.

EXAMPLE 9

A. A 200 mg sample of the succinoylated-PEI-PrSi-silica gel obtained form Example 7A is packed between 2 polyethylene 20 microliter pore size frits in a 1 ml polypropylene syringe barrel. 2 Milliliters of 0.01M potassium phosphate buffer, pH 6.6, are aspirated through the column at a vacuum of 20 in. Hg by means of a vacuum manifold commercially available under the brand name Baker-10 SPE ™ System, J. T. Baker Chemical Co., Phillipsburg, N.J. A 100 microliter sample of hybridoma tissue culture media supernatant containing immunoglobulin G of unknown specificity is clarified by centrifugation and then diluted with 400 microliters of 0.01M potassium phosphate buffer, pH 6.6. The entire 500 microliter sample is applied to the column on the Baker-10 SPE ™ System at a vacuum pressure of 20 in. Hg. The eluate is collected. The column is washed with 4 mls 0.01M potassium phosphate, pH 6.6, and the eluate is collected. The column is washed with 2 mls 0.035M potassium phosphate, pH 6.6, and finally with 2 mls 0.1M potassium phosphate, pH 6.6. In each wash, the eluate is collected. Each of the collected elutes is analyzed by sodium dodecyl sulfate polyacrylamide gel electrophoresis, performed essentially as described by U.K. Laemmli, Nature, 227, 680 (1970). The 0.010M potassium phosphate, pH 6.6, eluate contains the albumin, transferrin, and most of the other proteins of the original sample, excluding immunoglobulin G. The quantitatively recovered immunoglobulin G, along with approximately 10% contaminating protein, is found in the 0.1M potassium phosphate, pH 6.6, eluate.

B. Similar recovery of immunoglobulin G is obtained by following the procedure of Example 9A with a 100 microliter sample of human serum.

C. An equivalent amount of the glutaroyl-PEI-PrSi-silica gel and the diglycoloyl-PEI-PrSi-silica gel of Example 7B is each substituted for the succinoyl-PEI-PrSi-silica gel in the process of Example 9A to provide similar recovery of immunoglobulin G.

EXAMPLE 10

A. A stainless steel chromatographic column, 25 cm ×0.46 mm, is packed with 3.8 grams of the succinoylated-PEI-PrSi-silica gel of Example 6 and equilibrated with 0.01M potassium phosphate buffer, pH 6.0, by pumping this buffer through the column at a flow rate of 1 ml/min for 20 minutes. A 0.1 milliliter sample of human plasma is applied to the packed column and protein separation is achieved by gradient elution using a 120 minute linear gradient from 0.01M potassium phosphate, pH 6.0, to 0.25M potassium phosphate, pH 6.8, at a flow rate at 1 ml/min. Protein elution is detected using UV absorbance at 280 nm with full scale absorbance set at 0.32 absorbance units. A series of 280 nm absorbing peaks are detected ranging in retention time from about 2 minutes to about 50 minutes. The protein peak at about 25 minutes retention time is identified as the human plasma IgG fraction by a co-chromatographing with a commercially available sample of human IgG antibody, obtained from Miles Laboratories, Inc., Naperville, IL under Catalog No. 641451, using the identical gradient profile as outlined above. The protein peak eluting at about 25 minutes is evaluated to be greater than 70% pure by sodium dodecyl sulfate polyacrylamide gel electrophoresis, as described by U.K. Laemmli, Nature, ibid., which gives two major Coomassie blue bands corresponding to molecular weight of 50,000 daltons (heavy chain of IgG) and 25,000 daltons (light chain of IgG) and several faint Coomassie blue bands representing less than 30% of the total stained protein. Recovery of the IgG antibody is greater than 90%.

B. The procedure of Example 10A is repeated twice, except that a 1.0 ml sample of mouse ascites fluid containing IgG antibody, in particular IgG antibody with specificity for bovine serum albumin and IgG antibody with specity for sheep red blood cels, respectively, is substituted for the 0.1 ml sample of human plasma utilized therein. The peak retention time for the former sample is 26 minutes and for the latter 30 minutes. The analyzed percent purity and the recovery of the extracted IgG in both samples is greater than 90%.

C. The procedure of Example 10A is repeated, except that a 1.0 ml sample of hybridoma tissue culture media supernatant containing IgG antibody of unknown specificity is substituted for the 0.1 ml sample of human plasma. The peak retention time is 45 minutes; and the analyzed purity and recovery are each greater than 90%.

EXAMPLE 11

A. To 1.0 mililiter of hybridoma tissue culture media supernatant and 3.0 mls of 0.01M potassium phosphate buffer, pH 6.0, is added 30.0 mg of the succinoylated-PEI-PrSi-silica gel bonded phase from Example 8. This mixture is shaken for 1 minute. The bonded phase is allowed to settle for 1 hour and the resulting supernatant is decanted. The solid residue is resuspended by shaking in 10 mls of 0.01M potassium phosphate buffer, pH 6.0, and allowed to settle for 1 hour. This second supernatent is then decanted, and the solid residue therefrom is resuspended by shaking in 1.0 ml of 0.125M potassium phosphate buffer, pH 6.8, for 1 minute and this mixture is again allowed to settle for 1 hour. The resulting supernatant is decanted. Each of the three supernatant fluids are analyzed by HPLC chromatography and the previously noted sodium dodecyl sulfate polyacrylamide gel electrophoresis. The fluid supernatant is found to contain more than 75% of the IgG antibody present within the original sample at greater than 90% purity. The other two supernatants are found to contain less than 5% of the IgG antibody. Additional IgG also can be recovered from the solid phase material by re-extraction with 0.125M potassium phosphate buffer, pH 6.8.

B. The procedure of Example 11A is repeated except that an equivalent amount of the succinoylated-PEI-PrSi-CPG of Example 5B is substituted for the succinoylated-PEI-PrSi-silica gel used therein with substantially the same results.

We claim:

1. A method of obtaining substantially purified immunoglobulin G from a sample of biological fluid containing said immunoglobulin G which comprises separating and recovering said immunoglobulin G from said sample by employing liquid chromatography or solid phase extraction wherein the chromatographic packing or solid phase matrix, respectively, consists essentially of the carboxylated covalently bound, non-crosslinked polyethylenimine reaction product of particulate silica gel having an average particle diameter of from about 3 to about 70 microns and an average pore size of from about 50 to about 1000 Angstrom units, or particulate controlled pore glass having an average particle diameter of from about 37 to about 177 microns and an average pore size of from about 40 to about 1000 Angstrom units, with polyethyleniminopropyl trimethoxy silane having an average molecular weight of from about 400 to about 1800.

2. In the method of claim 1, said carboxylated reaction product having a carboxyl milliequivalent per gram of product of from about 0.3 to about 1.2.

3. In the method of claim 2, said biological fluid being plasma, serum, tissue culture supernatant or ascites fluid.

4. A method of obtaining substantially purified immunoglobulin G from a sample of biological fluid containing said immunoglobulin G which comprises separating and recovering said immunoglobulin G from said sample by employing liquid chromatography or solid phase extraction wherein the chromatographic packing or solid phase matrix, respectively, consists essentially of the carboxylated covalently bound, non-crosslinked polyethylenimine reaction product of particulate silica gel having an average particle diameter of from about 3 to about 70 microns and an average pore size of from about 50 to about 1000 Angstrom units with polyethyleniminopropyl trimethoxy silane having an average molecular weight of from about 400 to about 1800.

5. In the method of claim 4, said carboxylated reaction product having a carboxyl milliequivalent per gram of product of from about 0.3 to about 1.2.

6. In the method of claim 5, said biological fluid being plasma, serum, tissue culture supernatent or ascites fluid.

7. A method of obtaining substantially purified immunoglobulin G from a sample of biological fluid containing said immunoglobulin G which comprises separating and recovering said immunoglobulin G from said sample by employing liquid chromatography or solid phase extraction wherein the chromatographic packing or solid phase matrix, respectively, consists essentially of the carboxylated covalently bound, non-crosslinked polyethylenimine reaction product of particulate controlled pore glass having an average particle diameter of from about 37 to about 177 microns and an average pore size of from about 40 to about 1000 Angstrom units, with polyethyleniminopropyl trimethoxy silane having an average molecular weight of from about 400 to about 1800.

8. In the method of claim 7, said carboxylated reaction product having a carboxyl milliequivalent per gram of product of from about 0.3 to about 1.2.

9. In the method of claim 8, said biological fluid being plasma, serum, tissue culture supernatent or ascites fluid.

10. A method of obtaining substantially purified immunoglobulin G from a sample of biological fluid containing said immunoglobulin G which comprises:

a. equilibrating said sample of biological fluid to an ionic strength equal to or less than the ionic strength of the lower ionic strength buffer used for gradient elution in the subsequent chromatographic separation and recovery step and to a pH greater than the pI of the particular immunoglobulin G, and b. separating and recovering said immunoglobulin G from said sample by employing liquid chromatography wherein the chromatographic packing consists essentially of the carboxylated covalently bound, non-crosslinked reaction product of particulate silica gel having an average particle diameter of from about 3 to about 70 microns and average pore size of from about 50 to about 1000 Angstrom units, or particulate controlled pore glass having an average particle diameter of from about 37 to about 177 microns and an average pore size of from about 40 to about 1000 Angstrom units, with polyethyleniminopropyl trimethoxy silane having an average molecular weight of from about 400 to about 1800.

11. In the method of claim 10, said carboxylated reaction product having a carboxyl milliequivalent per gram of product of from about 0.3 to about 1.2.

12. In the method of claim 11, said biological fluid being plasma, serum, tissue culture supernatent or ascites fluid.

* * * * *